United States Patent
Hu et al.

(10) Patent No.: US 11,779,534 B2
(45) Date of Patent: Oct. 10, 2023

(54) FILM-FORMING COSMETIC COMPOSITION COMPRISING POLYURETHANE AND CROSS-LINKED STARCH

(71) Applicant: L'OREAL, Paris (FR)

(72) Inventors: Echo Xiaoying Hu, Shanghai (CN); Daniel Chen, Shanghai (CN)

(73) Assignee: L'OREAL, Paris (FR)

( * ) Notice: Subject to any disclaimer, the term of this patent is extended or adjusted under 35 U.S.C. 154(b) by 108 days.

(21) Appl. No.: 17/255,596

(22) PCT Filed: Jun. 28, 2018

(86) PCT No.: PCT/CN2018/093228
§ 371 (c)(1),
(2) Date: Dec. 23, 2020

(87) PCT Pub. No.: WO2020/000284
PCT Pub. Date: Jan. 2, 2020

(65) Prior Publication Data
US 2021/0154128 A1    May 27, 2021

(51) Int. Cl.
| | |
|---|---|
| A61K 8/87 | (2006.01) |
| A61K 8/19 | (2006.01) |
| A61K 8/34 | (2006.01) |
| A61K 8/362 | (2006.01) |
| A61K 8/365 | (2006.01) |
| A61K 8/40 | (2006.01) |
| A61K 8/41 | (2006.01) |
| A61K 8/44 | (2006.01) |
| A61K 8/46 | (2006.01) |
| A61K 8/73 | (2006.01) |
| A61K 8/85 | (2006.01) |
| A61Q 17/00 | (2006.01) |
| A61Q 19/00 | (2006.01) |

(52) U.S. Cl.
CPC .............. *A61K 8/87* (2013.01); *A61K 8/19* (2013.01); *A61K 8/345* (2013.01); *A61K 8/362* (2013.01); *A61K 8/365* (2013.01); *A61K 8/40* (2013.01); *A61K 8/41* (2013.01); *A61K 8/44* (2013.01); *A61K 8/466* (2013.01); *A61K 8/732* (2013.01); *A61K 8/85* (2013.01); *A61Q 17/00* (2013.01); *A61Q 19/00* (2013.01); *A61K 2800/30* (2013.01); *A61K 2800/33* (2013.01)

(58) Field of Classification Search
None
See application file for complete search history.

(56) References Cited

U.S. PATENT DOCUMENTS

| | | | |
|---|---|---|---|
| 6,248,338 B1 * | 6/2001 | Muller | A61Q 11/00 424/70.13 |
| 2011/0015279 A1 | 1/2011 | Doerr | |
| 2011/0150805 A1 * | 6/2011 | Kergosien | A61K 8/04 424/78.03 |

FOREIGN PATENT DOCUMENTS

| | | |
|---|---|---|
| CN | 104352359 A | 2/2015 |
| CN | 105816351 A | 8/2016 |
| CN | 105885660 A | 8/2016 |
| CN | 106243964 A | 12/2016 |
| CN | 108078959 A | 5/2018 |
| FR | 2838335 A1 | 10/2003 |
| WO | WO 2018/064677 A1 | 4/2018 |

OTHER PUBLICATIONS

Ding Tong et al.—1994 Comments of relevance in English attached.
Xiaowei—2007, ISBN 978-7-5019-5753-8, http://www.chlip.com.cn, Comments of relevance in English attached.

* cited by examiner

*Primary Examiner* — Kyung S Chang
(74) *Attorney, Agent, or Firm* — POLSINELLI PC

(57) ABSTRACT

A cosmetic composition comprising, in an aqueous cosmetically acceptable medium: a) from 6% to 50% by weight in active material of at least one aqueous polyurethane dispersion; and b) from 2% to 8% by weight of at least one cross-linked starch, the weight being expressed by weight of the total weight of the composition.

17 Claims, No Drawings

FILM-FORMING COSMETIC COMPOSITION COMPRISING POLYURETHANE AND CROSS-LINKED STARCH

CROSS REFERENCE TO RELATED APPLICATIONS

This application is a National Phase filing under 35 U.S.C. § 371 of PCT/CN2018/093228 filed on Jun. 28, 2018, the entire contents of which are hereby incorporated by reference.

The present invention concerns a cosmetic composition comprising, in an aqueous cosmetically acceptable medium:
a) from 6% to 50% by weight in active material of at least one aqueous polyurethane dispersion; and
b) from 2% to 8% by weight of at least one cross-linked starch,
the weight being expressed by weight of the total weight of the composition.

The human skin and scalp is the first barrier protecting the body from the environment. Every day it undergoes external aggressions, which result in many skin problems, such as accelerated aging, skin disorder, discomfort, or skin greasiness. The external aggressions are caused for example, by UV radiation or atmospheric pollution.

In particular, atmospheric pollution, namely the pollutants in the air, has raised increasing concerns of the consumers, due to its adverse impact to the skin. Among different types of pollutants existing in the air, dust or fine particles or gases, have been raising attentions of the consumers, in particular since recent years.

Fine particles existing in the air tend to be adherent to the skin. They will deposit on the skin even after cleansing. This deposition is not desired by the consumers, as it is believed that the pores on the skin will be clogged and therefore causing skin problems.

However, the conventional arts did not disclose or provide a solution for preventing or reducing the deposition of fine particles on the skin and scalp.

There thus exists a need for formulating a composition which protects the skin and scalp from polluted air. There is also a need for providing a composition which forms a film on skin which is easy to peel off, and which is for long-wear skin application and fast forming. Besides, said film has to be breathable and moderate waterproof. Such a film would be used as a second skin to protect skin from the polluted air.

The Applicant has now discovered that it is possible to formulate a cosmetic composition having the desired properties as described above. Specifically, the Applicant has discovered that it is possible to formulate a skin care composition, which is easy to peel off, long-wear and fast forming. Said film is used as a second skin to protect skin from the polluted air, and offers skin care treatment when corresponding active agents are present at the same time.

The present invention thus relates to a cosmetic composition comprising, in an aqueous cosmetically acceptable medium:
a) from 6% to 50% by weight in active material of at least one aqueous polyurethane dispersion; and
b) from 2% to 8% by weight of at least one cross-linked starch.

Unless mention of the contrary, the percentages are expressed by weight of the total weight of the composition.

Other subjects and characteristics, aspects and advantages of the invention will emerge even more clearly on reading the description and the examples that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

The composition of the invention is intended for dermal application: it is applied on skin and/or scalp.

As shown in the examples, it could be moldable on skin, and quickly forms an invisible/visible film after 1-2 minutes of drying time. The film provides skin protection with flexible, breathable, non-tacky, long wearing and moderate waterproof properties. The film can be peeled off directly from skin.

Moreover, the combination of cross-linked starch with polyurethane enhances the water resistance of the polyurethane film, while improving the film affinity to skin and retaining the flexibility of polyurethane film.

The present invention also relates to a cosmetic method for caring the skin and/or scalp, comprising the application to said skin and/or scalp of a composition of the invention.

It also relates to the use of a composition of the invention for caring the skin and/or scalp.

Aqueous Polyurethane Dispersion

According to the present invention, the composition comprises at least one aqueous polyurethane dispersion.

"Aqueous polyurethane dispersion" as used herein means the aqueous polyurethane dispersions disclosed in U.S. Pat. Nos. 7,445,770 and/or 7,452,770, the entire contents of both of which are hereby incorporated by reference.

More specifically, the aqueous polyurethane dispersions of the present invention are preferably the reaction products of:
A) a prepolymer according to the formula:

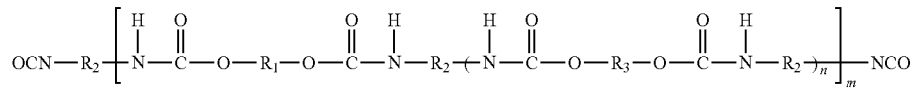

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;
B) at least one chain extender according to the formula: $H_2N-R_4-NH_2$ wherein $R_4$ represents an alkylene or alkylene oxide radical not substituted with ionic or potentially ionic groups; and C) at least one chain extender according to the formula: $H_2N-R_5-NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate, dicyclohexylmethane diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, hexylene glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the content of which is hereby incorporated by reference. Preferred compounds include dimethylol butanoic acid (DMBA), dimethylol propionic acid (DMPA), adipic acid and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is a chain extended using two classes of chain extenders. First, compounds having the formula: $H_2N-R_4-NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders corresponds to compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS), the sodium salt of N-(2-aminoethyl)-3-aminoethane sulfonic acid or the sodium salt of N-(2-aminoethyl)-2-aminopropionic acid.

The polyurethane according to the invention may also include compounds which are situated in each case at the chain ends and terminate said chains (chain terminators) as described in U.S. Pat. No. 7,445,770 and/or U.S. Pat. No. 7,452,770.

Preferably, the aqueous polyurethane dispersion has a viscosity of less than 2000 mPa·s at 23° C., preferably less than 1500, preferably less than 1000. Further preferably, the aqueous polyurethane dispersion has a glass transition temperature below 0° C.

Also preferably, the aqueous polyurethane dispersion has a solid content based on the weight of the dispersion of from 20% to 60%, preferably from 25% to 55% and preferably from 30% to 55%.

Suitable aqueous polyurethane dispersions for use in the present invention include, but are not limited to, aqueous polyurethane dispersions sold under the BAYCUSAN® name by Covestro (formerly Bayer) such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35); or sold by Wanhua Chemical Group Co., Ltd under the name CARFIL 9235 (polyurethane-2).

Preferably, the polyurethane is a copolymer of adipic acid, dicyclohexylmethane diisocyanate, ethylenediamine, hexane diol, neopentyl glycol and sodium N-(2-aminoethyl)-3-aminoethanesulfonate monomers.

Preferably, the polyurethane is different from the interpenetrated polymer network (IPN) of a polyurethane and a poly(meth)acrylate. As used herein, the expression "interpenetrated polymer network" refers to a blend of two interlaced polymers, obtained by simultaneous polymerization and/or crosslinking of two types of monomer, the blend obtained having a single glass transition temperature. Preferably, the polyurethane is different from the IPNs that are commercially available from the company Evonik under the name Hybridur. Preferably the IPN is different from the one of Evonik available under the trade name Hybridur 875 (INCI name: POLYURETHANE-2 (and) POLYMETHYL METHACRYLATE).

Preferably, the polyurethane of the invention does not comprise any poly(meth)acrylate polymer.

The aqueous polyurethane dispersion is present in the composition of the present invention, in active material, in an amount ranging from about 6 to 50% by weight (non-dry weight basis), more preferably from about 6.5 to about 45% by weight, more preferably from about 6.5 to about 40% by weight based on the total weight of the composition.

Cross-Linked Starch

The composition of the invention also comprises from 2% to 8% by weight of at least one cross-linked starch. Said cross-linked starch is also called modified starch.

Starch(es) that can be used in this invention are particularly macromolecules in the form of polymers composed of elementary patterns that are anhydroglucose units. The number of these patterns and their assembly provide a means of distinguishing amylose (linear polymer) and amylopectin (ramified polymer). The relative proportions of amylose and of amylopectin, as well as their degree of polymerization, vary according to the plant origin of the starches.

The starch molecules used in this invention may originate from a plant source such as cereals, tubercles, roots, vegetables and fruits. Thus, the starch(es) may originate from a plant source chosen from among maize, peas, potatoes, sweet potatoes, banana, barley, wheat, rice, oat, sago, tapioca and sorghum. The starch is preferably derived from potatoes.

Hydrolysates from starches mentioned above may also be used.

Starches are usually in the form of a white powder, insoluble in cold water, with an elementary particle size varying from 3 to 100 microns.

The starches used in the composition according to the invention are chemically modified by cross-linking. In particular, these reactions may be performed by cross-linking by functional agents capable of reacting with hydroxyl groups of starch molecules that will thus be bonded to each other (for example with glyceryl and/or phosphate groups).

In particular, monostarch phosphates (of the Am-O—PO—(OX)2 type), distarch phosphates (of the Am-O—PO—(OX)—O-Am type) or even tristarch phosphates (of the Am—O—PO—(O-Am)2 type) or mixes of them may be obtained by cross linking with phosphorated compounds.

In particular, X denotes alkaline metals (for example sodium or potassium), alkaline earth metals (for example calcium, magnesium), ammonia salts, amine salts like monoethanolamine, diethanolamine, triethanolamine, amino-3 propanediol-1,2 salts, ammonium salts derived from basic aminoacids like as lysine, arginine, sarcosine, ornithine, citrulline.

The phosphorated compounds may for example be sodium tripolyphosphate, sodium orthophosphate, phosphorus oxichloride or sodium trimetaphosphate.

Distarch phosphates will be in particular used, or compounds rich in distarch phosphate such as the product marketed under references PREJEL VA-70-T AGGL (gelatinized hydroxypropylated manioc distarch phosphate) or PREJEL TK1 (gelatinized manioc distarch phosphate) or PREJEL 200 (gelatinized acetylated manioc distarch phosphate) by the AVEBE Company or STRUCTURE ZEA or STRUCTURE XL by the Akzo Nobel (gelatinized hydroxypropylated maize distarch phosphate).

Preferably, the cross-linked starch is a gelatinized hydroxypropylated maize distarch phosphate.

Amphoteric starches can also be used in the invention; these amphoteric starches contain one or several anionic groups and one or several cationic groups. The anionic and cationic groups may be related to the same reactive site of the starch molecule or to different reactive sites, but they are preferably related to the same reactive site. The anionic groups may be of the carboxylic, phosphate or sulfate type, and preferably carboxylic. Cationic groups may be of the primary, secondary, tertiary of quaternary amine type.

Amphoteric starches are chosen particularly from among compounds with the following formulas:

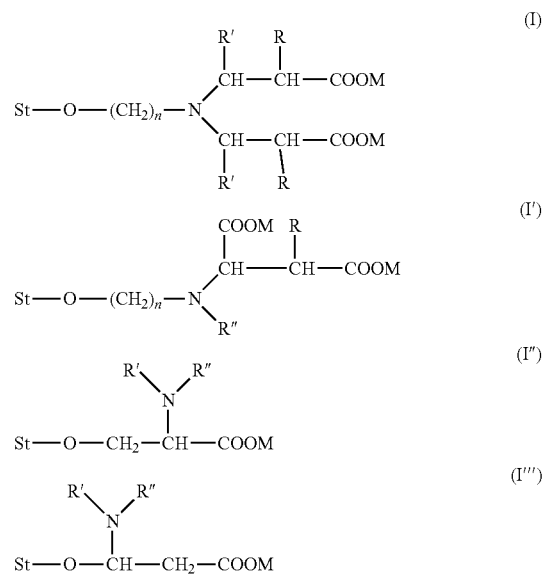

formulas in which:
St-O represents a starch molecule,
R, identical or different, represents a hydrogen atom or a methyl group,
R', identical or different, represents a hydrogen atom, a methyl group or a —COOH group,
n is an integer equal to 2 or 3,
M, identical or different, denotes a hydrogen atom, an alkali metal or alkali earth metal such as Na, K, Li, NH$_4$, a quaternary ammonium or an organic amine,
R" represents a hydrogen atom or an alkyl group having from 1 to 18 carbon atoms.

These compounds are described particularly in U.S. Pat. Nos. 5,455,340 and 4,017,460 which are included as references.

As amphoteric starches, the starches having formulas (I) or (I') will in particular be used. In particular, potato starches modified by 2-chloroethyl aminodipropionic acid, i.e. starches of formula (I) or (I') are used in which R, R', R" and M are a hydrogen atom and n is equal to 2. Mention can be made in particular of potato starch modified by 2-chloroethyl aminodipropionic acid neutralized with soda, marketed under the reference STRUCTURE SOLANACE by NATIONAL STARCH.

O-carboxymethylated starch designates a starch that has been modified by substitution, in the free hydroxyl groups, of a hydrogen with a carboxymethylated group —CH2COOH. It can be as such, or in the form of salt, for example an alkali metal salt.

O-carboxymethylated starches can be prepared, for example, by reacting a starch with monochloroacetic acid, or a monochloroacetic acid alkali salt (for example sodium salt).

Preferably, and O-carboxymethylated starch is used that has the form of an alkali metal salt, and more preferably, in the form of a sodium salt.

Preferably, the O-carboxymethylated starch is prepared using potato starch.

The O-carboxymethylated starch can also be partially or entirely cross-linked. Preferably, it is partially cross-linked. The cross-linking of the starch can be carried out for example by heating the starch, or by having it react with cross-linking agents such as phosphates, glycerol.

Even more preferably, the O-carboxymethylated starch is a sodium salt of starch, in particular of potato, O-carboxymethylated and partially cross-linked. Such a product is for example marketed under the name PRIMOJEL by AVEBE.

The cross-linked starch is present in the composition in a content ranging from 2% to 8% by weight, preferably from 3% to 7.5% by weight and preferably from 4% to 6% by weight in relation to the total weight of the composition.

Preferably, the weight ratio (polyurethane: cross-linked starch) is comprised between 1 and 7, preferably between 1.1 and 6.5.

The composition according to the invention also comprises an aqueous medium.

Aqueous Medium

The composition according to the invention comprises an aqueous phase (i.e. an aqueous cosmetically acceptable medium).

According to a particular embodiment, the composition comprises a quantity of water from 30% to 95% by weight, preferably from 54% to 87% by weight, and preferably from 60% to 85% by weight in relation to the total weight of the composition.

The water used can be sterile demineralized water and/or floral water such as rose water, cornflower water, chamomile water or linden water, and/or a spring or natural mineral water, such as for example: Vittel water, water from the basin of Vichy, Uriage water, la Roche Posay water, la Bourboule water, Enghien-les-Bains water, Saint Gervais-les-Bains water, Néris-les-Bains water, Allevar-les-Bains water, Digne water, Maizières water, Neyrac-les-Bains water, Lons-le-Saunier water, les Eaux Bonnes, Rochefort water, Saint Christau water, Fumades water and Tercis-les-bains water, Avene water.

The aqueous phase may comprise at least one solvent miscible with water. Said solvent may be chosen from polyols and alcohols, such as glycerin, sorbitol, glycols such as butylene glycol, propylene glycol, isoprene glycol, dipropylene glycol, hexylene glycol, polypropylene glycol, ethanol or propanediol.

The composition of the invention may comprise additional ingredients. Said additional ingredient can be, for example, any colorant (pigment, dye . . . ) and/or any pharmaceutically or cosmetically active agent.

Moreover, a makeup product could be applied onto the film. Depending on its use, functional active agents for skin treatment, such as UV filters, anti-oxidants, antispot agents, anti-acne agents and/or anti-wrinkle agents could be loaded on the film.

Preferably, the composition of the invention comprises hydrophobic particles. The hydrophobic particles may be chosen from hydrophobic silica aerogel particles, titanium dioxide and talc.

Aerogel Particles of Hydrophobic Silica

The composition according to the invention preferably comprises hydrophobic silica aerogel particles.

Aerogels are ultra-lightweight porous materials, the first of which were made by Kristler in 1932.

They are generally synthesized by a sol-gel method in a liquid medium then dried by extraction of a supercritical fluid. The most commonly used supercritical fluid is supercritical CO2. This type of drying makes it possible to prevent contraction of the pores and of the material. There are other types of drying that can also be used to obtain porous materials starting from a gel, for example (i) drying by cryodessiccation, consisting of solidifying the gel at low temperature and then sublimating the solvent and (ii) drying by evaporation. The materials thus obtained are called cryogels and xerogels respectively. The sol-gel method and the various dryings are described in detail in Brinker C J., and Scherer G. W., Sol-Gel Science: New York: Academic Press, 1990.

"Hydrophobic silica" denotes any silica for which the surface is treated by silylation agents, for example by halogenated silanes such as alkylchlorosilanes; silanes and particularly dimethylsiloxanes such as hexamethyldisiloxane; or silazanes, so as to functionalize OH groups by Si—Rn silyl groups, for example trimethylsilyl groups.

Preferably, aerogel particles of hydrophobic silica that could be used in this invention advantageously have a specific area per unit mass (SM) varying from 500 to 1500 $m^2/g$, preferably from 600 to 1200 $m^2/g$ and even better from 600 to 800 $m^2/g$.

Preferably, aerogel particles of hydrophobic silica that could be used in this invention advantageously have an oil absorption capacity measured at the WET POINT varying from 5 to 18 ml/g of particles, preferably from 6 to 15 ml/g and better from 8 to 12 ml/g.

Preferably, aerogel particles of hydrophobic silica that could used in this invention advantageously have a size, expressed as an average diameter (D[0.5]), less than 1500 µm and preferably varying from 1 to 1000 µm, preferably from 1 to 100 µm, even better from 1 to 30 µm, preferably from 5 to 25 µm, even better from 5 to 20 µm and even better again from 5 to 15 µm.

Preferably, aerogel particles of hydrophobic silica that could used in this invention advantageously have a compacted density p varying from 0.04 $g/cm^3$ to 0.10 $g/cm^3$, and preferably from 0.05 $g/cm^3$ to 0.08 $g/cm^3$.

Preferably, aerogel particles of hydrophobic silica that could be used in this invention advantageously have a specific area per unit volume (SV) varying from 5 to 60 $m^2/cm^3$, preferably from 10 to 50 $m^2/cm^3$ and even better from 15 to 40 $m^2/cm^3$.

According to one preferred embodiment, the aerogel particles of hydrophobic silica according to the invention have a specific area per unit mass (SM) varying from 500 to 1500 $m^2/g$, preferably from 600 to 1200 $m^2/g$ and even better from 600 to 800 $m^2/g$, and a size expressed as an average diameter (D[0.5]) varying from 1 to 30 μm and/or an oil absorption capacity measured at the WET POINT varying from 5 to 18 ml/g of particles, preferably 6 to 15 ml/g and even better from 8 to 12 ml/g.

According to another preferred embodiment, the aerobic particles of hydrophobic silica used in this invention have a specific area per unit mass (SM) varying from 600 à 800 m²/g and a size expressed as an average diameter in volume (D[0.5]) varying from 5 to 20 μm, and better from 5 to 15 μm.

The specific area per unit mass may be determined using the nitrogen absorption method called the BET (BRUNAUER-EMMET-TELLER) method described in "The journal of the American Chemical Society", vol. 60, page 309, February 1938 and corresponding to international standard ISO 5794/1 (Appendix D). The BET specific area is the total specific area of the particles considered.

The absorption capacity measured at the WET POINT and denoted Wp, corresponds to the quantity of oil that must be added to 100 g of particles in order to obtain a homogeneous paste. It is measured using the Wet Point method or the method for determining oil take-up of powder according to the principle described in standard NF T 30-022. It corresponds to the quantity of oil adsorbed on the available surface of the powder and/or absorbed by the powder according to the Wet Point measurement, as described below:

A quantity m=2 g of powder is placed on a glass plate and oil (isononyl isononanoate) is then added drop by drop. After adding 4 to 5 drops of oil into the powder, it is mixed using a spatula and the addition of oil is continued until oil and powder conglomerates are formed. After this stage, oil is added one drop at a time and the mixture is then triturated with the spatula. The addition of oil is stopped when a firm and smooth paste is obtained. This paste should be allowed to spread on the glass plate without crazing and without the formation of lumps. The volume Vs (expressed in ml) of oil used is then noted.

The oil take-up (oil absorption capacity) corresponds to the Vs/m ratio.

The sizes of aerogel particles according to the invention can be measured by static diffusion of light by means of a commercial Malvern MasterSizer 2000 granulometer. Data are processed based on Mie's scattering theory. This theory, precise for isotropic particles, can determine an "effective" particle diameter in the case of non-spherical particles. This theory is described particularly in the book by Van de Hulst, H. C., "Light Scattering by Small Particles", Chapters 9 and 10, Wiley, New York, 1957.

In the framework of this invention, the compacted density can be evaluated using the following protocol called the compacted density protocol: 40 g of powder is poured into a graduated test tube and the test tube is then placed on a STAV 2003 apparatus made by STAMPF VOLUMETER. A series of 2500 compactions is then applied to the test tube (this operation is repeated until the difference in volume between two successive compactions is less than 2%); the final volume Vf of compacted powder is then measured on the test piece directly. The compacted density is then determined by the mass(m)A/f, ratio, in fact 40/Vf (where Vf is expressed in cm³ and m is expressed in g).

The specific area per unit volume is given by the relation: $SV=SM \times p$, in which p is the compacted density expressed in g/cm³ and SM is the specific area per unit mass expressed in m²/g, as defined above.

Aerogel particles of hydrophobic silica used according to this invention are preferably aerogel particles of silica silylate (INCI name).

The preparation of aerogel particles of hydrophobic silica modified on the surface by silylation is described earlier in document U.S. Pat. No. 7,470,725.

Particles of hydrophobic silica aerogels modified on the surface by trimethylsilyl groups will be used in particular.

Hydrophobic silica aerogels that can be used within the invention include for example the aerogel sold under the name VM-2260 (INCI name Silica silylate), by Dow Corning, of which the particles have an average size of about 1000 microns and a specific area per unit mass ranging from 600 to 800 m²/g.

Mention can also be made of the aerogels sold by Cabot under the references AEROGEL TLD 201, AEROGEL OGD 201 and AEROGEL TLD 203, ENOVA AEROGEL MT 1100, ENOVA AEROGEL MT 1200.

In particular, the aerogel sold under the name VM-2270 (INCI name Silica silylate), by Dow Corning, of which the particles have an average size ranging from about 5 to 15 microns and a specific area per unit mass ranging from 600 to 800 m²/g, will be used.

Compositions according to the invention can include a quantity of hydrophobic silica aerogel particles equal to between 0.01 and 3% by weight, preferably between 0.1 and 1% by weight, and even better between 0.2 and 0.5% by weight in relation to the total weight of the composition.

Preferably, the composition of the invention is substantially free of cationic surfactants and/or of any compound comprising at least one —$NH_3^+$ group.

By "substantially free", it is meant that the composition comprises less than 1% by weight, preferably less than 0.5% by weight, preferably less than 0.1% by weight of cationic surfactant and/or of any compound comprising at least one —$NH_3^+$ group. Preferably, the composition of the invention is devoid of cationic surfactant. Preferably, the composition of the invention is devoid of any surfactant. Preferably, the composition of the invention is devoid of any compound comprising at least one —$NH_3^+$ group.

Preferably, the composition of the invention is devoid of any compound chosen from Lauryl Methyl Gluceth-10 Hydroxypropyldimonium Chloride, Polyquaternium-59, Polyquaternium-37, Cetrimonium Chloride, Behentrimonium Chloride, Cetrimonium Bromide, Panthenyl Hydroxypropyl Steardimonium Chloride, Stearamidopropyl PG-dimonium Chloride Phosphate; Polyquaternium-10, Behentrimonium Methosulfate, Quaternium-91, Cetrimonium Methosulfate and Cinnamidopropyltrimonium Chloride. Preferably, the composition of the invention is devoid of all compounds which are Lauryl Methyl Gluceth-10 Hydroxypropyldimonium Chloride, Polyquaternium-59, Polyquaternium-37, Cetrimonium Chloride, Behentrimonium Chloride, Cetrimonium Bromide, Panthenyl Hydroxypropyl Steardimonium Chloride, Stearamidopropyl PG-dimonium Chloride Phosphate; Polyquaternium-10, Behentrimonium Methosulfate, Quaternium-91, Cetrimonium Methosulfate and Cinnamidopropyltrimonium Chloride.

The composition of the invention may comprise a non-ionic surfactant. Preferably, said non-ionic surfactant is an ethoxylated castor oil, preferably an ethoxylated hydrogenated castor oil. The moles of ethylene oxide per mole of castor oil will range from about 30 to about 55, preferably between about 37 and about 43, optimally about 40 moles of ethylene oxide. Most preferred non-ionic surfactant is PEG-40 hydrogenated castor oil. Preferably, said non-ionic surfactant is present in an amount of from 0.1% to 1% by weight, preferably from 0.2% to 0.8% by weight.

The present invention also relates to a cosmetic method for caring the skin and/or scalp, comprising the application to said skin and/or scalp of a composition of the invention.

It also relates to the use of a composition of the invention for caring the skin and/or scalp.

Preferably, the composition of the invention is for application onto skin and/or scalp, and not on hair.

The invention will be better understood after studying the following non-limitative examples that form preferred embodiments of the method conforming to the invention. Unless mentioned otherwise, quantities in the following examples are expressed as a percent by weight of the total weight of the composition (% w/w).

EXAMPLES

The following raw materials of Table 1 are used:

TABLE 1

| INCI | Composition | | Supplier and brand name |
|---|---|---|---|
| POLYURETHANE-34 | PU-34 | 32% | COVESTRO (BAYER) |
| (PU-34) | Water | 68% | BAYCUSAN C 1001 |
| POLYURETHANE-35 | PU-35 | 41% | COVESTRO (BAYER) |
| (PU-35) | Water | 59% | BAYCUSAN C 1004 |
| POLYURETHANE-32 | PU-32 | 50% | COVESTRO (BAYER) |
| (PU-32) | Water | 50% | BAYCUSAN C 1003 |
| POLYURETHANE-2 | PU-2 | 20.7% | EVONIK MATERIALS |
| (and) POLYMETHYL | PMMA | 19.7% | NETHERLANDS B.V. |
| METHACRYLATE | Dimethyl MEA | 0.9% | HYBRIDUR 875 |
| (PU-2 and PMMA) | Sodium dehydroacetate | 0.34% | POLYMER |
|  | Water | 58.360% | DISPERSION |
| PU-2 FILM FORMER | PU-2 | 35% | WANHUA CHEMICAL |
| (PU-2) | Water | 65% | GROUP CO., LTD CARFIL 9235 |
| HYDROXYPROPYL | HYDROXYPROPYL | 88% | AKZO NOBEL |
| STARCH PHOSPHATE | STARCH PHOSPHATE |  | STRUCTURE XL |
| (crosslinked starch) | Water | 12% |  |
| ACRYLATES/C10-30 | ACRYLATES/C10-30 ALKYL | 90% | LUBRIZOL |
| ALKYL ACRYLATE | ACRYLATE CROSSPOLYMER |  | CARBOPOL ULTREZ |
| CROSSPOLYMER | TRIDECETH-6 | 5% | 21 POLYMER |
|  | PEG-30 dipolyhydroxystearate | 5% |  |
| POLYACRYLATE | POLYACRYLATE | 100% | Seppic |
| CROSSPOLYMER-6 | CROSSPOLYMER-6 |  | SEPIMAX ZEN |

Example 1: Tests with Different Amounts of Polyurethanes (PU)

Formulas 1 to 4 of Table 2 are prepared by mixing PU-35 (Baycusan C 1004 of Covestro), in the quoted amounts, with 6% by weight hydroxypropyl starch phosphate (Structure XL) in water.

Each formula is applied evenly on to the back of the hand with an area of diameter of around 2 cm. After 1-2 min of drying process, pure water was sprayed on the applied area and polyurethane film is turned into white gradually. The possibility to pick up the resulting film in a piece was evaluated, and the continuity of the peeled off film was observed.

The results are in Table 2 below:

The legend of the table is as follows:

√: can pick up a film (peel off)/one piece film (film continuity)

X: cannot pick up a film (peel off)/cracking (film continuity)

TABLE 2

| No. | PU-35 (% of active material) | Hydroxypropyl starch phosphate | Peel off | Film continuity |
|---|---|---|---|---|
| 1 | 5% | 6% | x | X |
| 2 | 6.97% | 6% | √ | √ |
| 3 | 20.5% | 6% | √ | √ |
| 4 | 38.54% | 6% | √ | √ |

Thus, compositions comprising at least 6.97% by weight of PU-35 are able to form a film continuity with good peeling off.

Example 2: Tests with Different Amounts of Hydroxypropyl Starch Phosphate

Formulas 5 to 8 of Table 3 are prepared by mixing 20.5% by weight of active material of PU-35 (Baycusan C 1004 of Covestro) with hydroxypropyl starch phosphate (Structure XL), in quoted amounts, in water.

The resulting film is evaluated for water resistance and spreading.

For this purpose, each formula is applied evenly on to the back of the hand. The sensory of spreading was evaluated during application. After 1-2 min of drying process, pure water was sprayed on the applied area. The film color with residual water was observed to evaluate the water resistance.

The results are in Table 3 below:

The legend of the table is as follows:

Spreading: +++ very slippery, ++ slippery, + not so slippery, − not sliperry at all Water resistance: ++ transparent film & residual water droplet (the film repels water), + translucent film & residual water droplet (the film adsorbs water slowly), − white film (the film adsorbs water quickly).

TABLE 3

| No. | PU-35 (% of active material) | Hydroxypropyl starch phosphate | Water resistance | Spreading |
|---|---|---|---|---|
| 5 | 20.5% | 1% | − | +++ |
| 6 | 20.5% | 3% | + | ++ |

TABLE 3-continued

| No. | PU-35 (% of active material) | Hydroxypropyl starch phosphate | Water resistance | Spreading |
|---|---|---|---|---|
| 7 | 20.5% | 6% | ++ | + |
| 8 | 20.5% | 9% | ++ | − |

Thus, compositions comprising 3% to 6% by weight of hydroxypropyl starch phosphate (i.e. formulas 6 and 7) are able to show both water resistance and good spreading properties.

Example 3: Comparison Study of Films Comprising PU and Crosslinked Starch, and PU and Polyacrylate Derivatives Formulas 1 to 12 of Table 4 are prepared as indicated.
The resulting film is evaluated as follows:
Benefit 1: each formula was applied on a plastic plate by elcometer to form a film having a thickness of 50 μm. The film was put in the hood for drying during 24 hours.

Then the contact angle of MilliQ water on the film was measured by contact angle meter. For each formula, 15 μL of water was dropped to the film and the contact angle of this drop of water on the film was recorded immediately after contacting, which is CA0. After 5 min, the contact angle was recorded as CA5 min.

$$\Delta CA = CA0 - CA5 \text{ min.}$$

CA0, CA5ming and ΔCA are listed in Table 4 as benefit 1.
Benefit 2: film color was observed immediately after wetting. T=transparent, W=white.
Benefit 3: each formula was applied on the human skin, and the resulting film was evaluated for the flakiness appearance after rubbing (which mimics make up gesture).
Formulas 4, 6, 8 and 10-12 are comparative.
The results are in Table 4 below.
It results that the formulas according to the invention (1-3, 5, 7 and 9) are the only ones which provide all three benefits 1 to 3 at the same time.

TABLE 4

| | Formula | 1 | 2 | 3 | 4* | 5 | 6* | 7 | 8* | 9 | 10* | 11* | 12* |
|---|---|---|---|---|---|---|---|---|---|---|---|---|---|
| PU (% active material) | PU-35 (Baycusan C 1004 of Covestro) | 6.97% | 20.5% | 38.54% | 20.5% | | | | | | | | |
| | PU-34 (Baycusan C 1001 of Covestro) | | | | | 20.5% | 20.5% | | | | | | |
| | PU-32 (Baycusan C 1003 of Covestro) | | | | | | | 20.5% | 20.5% | | | | |
| | PU-2 (Carfil 9235 of Wanhua) | | | | | | | | | 20.5% | 20.5% | | |
| | PU-2 + PMMA (Hybridur 875 of Evonik) | | | | | | | | | | | 19.5% | 19.5% |
| | Hydroxypropyl starch phosphate (Structure XL) | 6% | 6% | 6% | | 6% | | 6% | | 6% | | 6% | |
| | Acrylates/C10-30 alkyl acrylate (Carbopal Ultrez-21) | | | | 1% | | | | | | 1% | | |
| | Polyacrylate crosspolymer-6 (Sepimax Zen) | | | | | | 2% | | 2% | | | | 2% |
| | Water | 77% | 44% | — | 49% | 30% | | | | | | | |
| Benefit 1 | CA0 | 75.4 | 76 | 76 | 67.8 | 81.6 | 40 | 75.6 | — | 71.7 | 73.3 | 33 | — |
| | CA5 min | 69.5 | 71.3 | 71.7 | 55 | 75.7 | — | 71.4 | — | 60.7 | 50.9 | — | — |
| | ΔCA | 5.9 | 4.7 | 4.3 | 12.8 | 5.9 | — | 4.2 | — | 11 | 22.4 | — | — |
| Benefit 2 | Color change immediately after wetting | T | T | T | W | T | W | T | W | T | W | T | — |

TABLE 4-continued

| Formula | | 1 | 2 | 3 | 4* | 5 | 6* | 7 | 8* | 9 | 10* | 11* | 12* |
|---|---|---|---|---|---|---|---|---|---|---|---|---|---|
| | | | | | | | Droplet collapsed after ~30 s | | Droplet immediately collapsed | | | Droplet collapsed after ~30 s | Continuous film not formed |
| Benefit 3 | Skin affinity (NO flakiness+, flakiness−) | + | + | + | − | + | − | + | − | + | − | + | − |

*= comparative formula

Example 4: Comparison Study of Viscosity Increase of Compositions Comprising PU and Crosslinked Starch Formulas 1 to 11, A, B and C of Table 5 are prepared as indicated.

Viscosity is evaluated as follows:

The measuring ladle of the viscosimeter RHEOMAT 180 is filled with the analyzed formula while preventing air from entering. The set to zero is done before measurement; then the viscosity of the formula is measured under the following parameters:
Mode: MANUAL
Measuring system: 75
Rotation speed: 200 rpm
The viscosity value is read after 10 minutes of rotation of the measuring instrument.

It corresponds to the following formula:
$$\text{Viscosity (measured)} = (K\text{tau} \times M)/R$$
wherein R=200 rpm,
Ktau=5.46 (for system 71 or M1), 54.77 (for system 72 or M2), 318 (for system 73 or M3), 1330.4 (for system 74 or M4), 5159.8 (for system 75).

In details, the inventors first calculate M in the above equation with Ktau (system 75, i.e. Ktau=5159.8) and measured viscosity.

Then, the real viscosity (in mPa.$) could be calculated with proper Ktau and M.

As illustration, if we take formula A of group 2, the measured viscosity with M2 was 20. Thus, by using the above formula, we obtain 20=(5159.8×M)/200, thus M=(20×200)/5159.8=0.775.

Then, real viscosity is equal to (54.77−proper Ktau for M2−x 0.775)/200=0.211 Pa·s, thus 211 mPa·s.

The results are in Table 5 below:

TABLE 5

| | | FLA | PU-35 (Baycusan C 1004) | PU-32 (Baycusan C 1003) | PU-2 (Carfil 9235) | PU-2 + PMMA (Hybridur 875 of Evonik) | Hydroxypropyl starch phosphate (Structure XL) | Acrylates/ C10-30 alkyl acrylate (Carbopol Ultrez-21) | Polyacrylate crosspolymer-6 (Sepimax Zen) |
|---|---|---|---|---|---|---|---|---|---|
| Group 1 | 1 | | | | | | 6% | | |
| | 2 | | | | | | | 1% | |
| | 3 | 20.5% | | | | | | | |
| | 4 | 20.5% | | | | | 6% | | |
| | 5 | 20.5% | | | | | | 1% | |
| Group 2 | A | 20.5% | | | | | | | |
| | 6 | | 20.5% | 6% | | | | | |
| | 7 | | 20.5% | | | | | | 2% |
| Group 3 | B | | 20.5% | | | | | | |
| | 8 | | | 20.5% | | | 6% | | |
| | 9 | | | 20.5% | | | | 1% | |
| Group 4 | C | | | | 19.5% | | | | |
| | 10 | | | | 19.5% | | 6% | | |
| | 11 | | | | 19.5% | 2% | | | |

| Formula | | Viscosity (mPa · S) |
|---|---|---|
| Group 1 | 1 | 2991 |
| | 2 | 4770 |
| | 3 | 94 |
| | 4 | 8689 |
| | 5 | 4641 |
| Group 2 | A | 211 |
| | 6 | 2413 |
| | 7 | 2163 |
| Group 3 | B | 163 |
| | 8 | 10907 |
| | 9 | 5853 |
| Group 4 | C | 103 |
| | 10 | 18307 |
| | 11 | 6059 |

The results show that the combination of PU-35 with hydroxypropyl starch phosphate (formula 4 in group 1) shows a higher viscosity than a formula comprising PU-35 dispersion only (formula 3 in group 1) and than a formula comprising hydroxypropyl starch phosphate-water dispersion only (formula 1 in group 1); this demonstrates that both ingredients together achieve a synergy on the increase of viscosity.

To the contrary, the combinations of polyurethane and acrylates/C10-30 alkyl acrylate (formulas 5 of group 1 and 9 of group 3) or of polyurethane and polyacrylate crosspolymer-6 (formulas 7 of group 2 and 11 of group 4) did not show the same way of synergy nor the same strength of viscosity.

Example 5: Comparison Study of Films Comprising PU and Crosslinked Starch, and PU and Polyacrylate Derivatives Formulas 1 to 12 of Table 4 are prepared as indicated.

The contact angle for each formula was measured as described in example 3. The peel off was evaluated as described in example 1.

The results are in Table 6 below.

It results that the formula according to the invention is the only one which provides peel off and the right contact angle.

TABLE 6

| Cream | Film-former | Formula | CA0 | CA5Min | Peel off |
|---|---|---|---|---|---|
| Second skin cream according to the invention | PU-35 + cross-linked starch | F1 | 82.1 | 76.3 | √ |
| Lotus cream | Sunspheres powder + silica + Emulium mellifera | F2 | 45 | — | x |
| Gel cream | CARBOMER | F3 | — | — | x |

| INCI | F2 (lotus cream) | F1 | F3 (gel cream) |
|---|---|---|---|
| SODIUM HYDROXIDE | | | 0.06 |
| TETRASODIUM EDTA | | | 0.2 |
| DISODIUM EDTA | 0.1 | | |
| SODIUM HYALURONATE | | | 0.01 |
| BETAINE (Genecare OSMS BA, Danisco) | | | 2 |
| DICAPRYLYL CARBONATE (Cetiol CC, Cognis) | 2 | | |
| SILICA | 1.5 | | |
| SILICA SILYLATE (VM-2270, Dow Corning) | | 0.5 | |
| FRAGRANCE | | | 0.14 |
| PVP (PVP K30L, ISP) | | 0.3 | |
| HYDROXYETHYLCELLULOSE (Natrosol 250 HHR CS, Ashland) | | 0.4 | |
| XANTHAN GUM (Keltrol CG, CP Kelco) | 0.2 | | |
| XANTHAN GUM (Keltrol CG-T, CP Kelco) | | | 0.05 |
| CARBOMER (Ashland 980 MS Carbomer, ashland) | | | 0.3 |
| ACRYLATES/C10-30 ALKYL ACRYLATE CROSSPOLYMER (Pemulen TR-1, Lubrizol) | | | 0.2 |
| AMMONIUM POLYACRYLOYLDIMETHYL TAURATE (Hostacerin AMPS, Clariant) | | | 0.2 |
| XANTHAN GUM (and) CERATONIA SILIQUA (CAROB) GUM (Nomcort CG, Nisshin Oillio) | | 0.05 | |
| STYRENE/ACRYLATES COPOLYMER (Sunspheres powder, Rohm & Haas) | 1 | | |
| AMMONIUM ACRYLOYLDIMETHYLTAURATE/STEARETH-25 METHACRYLATE CROSSPOLYMER (Aristoflex HMS, Clariant) | 0.9 | | |
| POLYURETHANE-35 (Baycusan C 1004) | | 50 | |
| HYDROXYPROPYL STARCH PHOSPHATE (Structure XL) | | 6 | |
| Preservatives | Qs | Qs | Qs |
| CYCLOHEXASILOXANE | 3 | | |
| DIMETHICONE (and) DIMETHICONOL | 1 | | |
| DIMETHICONE (and) DIMETHICONE/POLYGLYCERIN-3 | 1 | | |

TABLE 6-continued

| | | | |
|---|---|---|---|
| CROSSPOLYMER (KSG-710, Shin Etsu) | | | |
| ACRYLATES/POLYTRIMETHYLSILOXYMETH ACRYLATE COPOLYMER (Dowsil FA 4002 ID silicone acrylate, Dow Corning) | | 2 | |
| BUTYLENE GLYCOL | | | 7 |
| ALCOHOL | 3 | 5 | 5 |
| WATER | 58.3 | 32.35 | 69.0398 |
| GLYCERIN | 5 | 0.4 | 8 |
| PROPYLENE GLYCOL | 3 | | |
| CAPRYLYL GLYCOL | 0.3 | | |
| PROPANEDIOL | | 2.5 | |
| PEG-40 HYDROGENATED CASTOR OIL (Sympatens-TRH/400 (1), Kolb) | | 0.5 | |
| DISODIUM STEAROYL GLUTAMATE (Amisoft HS 21P, Ajinomoto) | 0.3 | | |
| POLYGLYCERYL-6 DISTEARATE (and) JOJOBA ESTERS (and) CETYL ALCOHOL (and) POLYGLYCERYL-3 BEESWAX (Emulium Mellifera MB, Gattefosse) | 3 | | |
| TOCOPHERYL ACETATE | 0.5 | | 0.5 |

The invention claimed is:

1. A cosmetic composition comprising, in an aqueous cosmetically acceptable medium:
   a) from about 6% to 50% by weight in active material of at least one aqueous polyurethane dispersion, wherein the at least one aqueous polyurethane dispersion is the reaction product of:
   A) a prepolymer according to the formula:

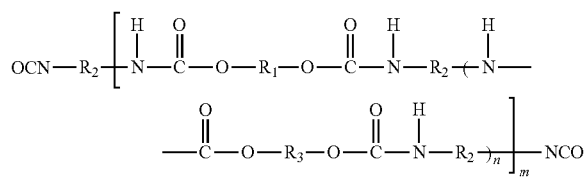

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;
   B) at least one chain extender according to the formula: $H_2N$—$R_4$—$NH_2$ wherein $R_4$ represents an alkylene or alkylene oxide radical not substituted with ionic or potentially ionic groups; and
   C) at least one chain extender according to the formula: $H_2N$—$R_5$—$NH_2$ wherein $R_5$ represents an alkylene radical substituted with an ionic group selected from diaminosulfonate groups; and
   b) from 2% to 8% by weight of at least one cross-linked starch selected from the group consisting of a gelatinized hydroxypropylated maize distarch phosphate, monostarch phosphates of the formula Am-O—PO—(OX)2, distarch phosphates of the formula Am-O—PO—(OX)—O-Am and tristarch phosphates of the formula Am-O—PO—(O-Am)2, wherein X denotes alkaline metals; alkaline earth metals, ammonia salts, amine salts; amino-3-propanediol-1,2 salts, ammonium salts derived from basic aminoacids and wherein Am is starch,
   the weight being expressed by weight of the total weight of the composition; wherein the weight ratio of the at least one aqueous polyurethane dispersion to the at least one cross-linked starch is between 1 and 7; and wherein the at least one aqueous polyurethane dispersion does not comprise any poly (meth)acrylate polymer.

2. The composition according to claim 1, wherein the polyisocyanate is an organic diisocyanate chosen from the group consisting of tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI), hydrogenated TDI, 4,4'-diisocyanato diphenyl methane and its isomeric mixtures with 2,4'- and optionally 2,2'-diisocyanato diphenylmethane, 1,5-diisocyanato naphthalene and dicyclohexylmethane diisocyanate.

3. The composition according to claim 1, wherein the low molecular weight diol is a diol having a molecular weight from about 62 to 700 and having up to about 20 carbon atoms per molecule, and is chosen from ethylene glycol, diethylene glycol, propane 1,2-diol, propane 1,3-diol, butane 1,4-diol, butylene 1,3-glycol, neopentyl glycol, hexylene glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), dimethylol butanoic acid (DMBA), dimethylol propionic acid (DMBA), adipic acid or carboxyl-containing caprolactone polyester diol.

4. The composition according to claim 1, wherein the at least one chain extender B) is an alkylene diamine chosen from the group consisting of hydrazine, ethylenediamine, propylenediamine, 1,4-butylenediamine and piperazine; or an alkylene oxide diamine chosen from the group consisting of 3-{2-[2-(3-aminopropoxy)ethoxy]ethoxy}propylamine, 2-methyl-1,5-pentanediamine, hexane diamine, isophorone diamine, and 4,4-methylenedi-(cyclohexylamine), dipropylamine propyleneglycol, dipropylamine dipropyleneglycol, dipropylamine tripropyleneglycol, dipropylamine poly (propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol.

5. The composition according to claim 1, wherein the at least one chain extender C) is chosen from the group consisting of the sodium salt of N-(2-aminoethyl)-2-aminoethane sulfonic acid, the sodium salt of N-(2-aminoethyl)-3-aminoethane sulfonic acid and the sodium salt of N-(2-aminoethyl)-2-aminopropionic acid.

6. The composition according to claim 1, wherein the at least one aqueous polyurethane dispersion is present in an amount, in active material, ranging from about 6.5 to about 45% by weight based on the total weight of the composition.

7. The composition according to claim 1, wherein the at least one cross-linked starch is selected from distarch phosphates of the formula Am-O—PO—(OX)—O-Am wherein X denotes sodium or potassium; calcium or magnesium; ammonia salts; monoethanolamine, diethanolamine, triethanolamine; amino-3 propanediol-1,2 salts; ammonium salts derived from lysine, arginine, sarcosine, ornithine, or citrulline.

8. The composition according to claim 1, wherein the at least one cross-linked starch is the gelatinized hydroxypropylated maize distarch phosphate.

9. The composition according to claim 1, wherein the at least one cross-linked starch is present in the composition in a content ranging from 3% to 7.5% by weight in relation to the total weight of the composition.

10. The composition according to claim 1, wherein the weight ratio of the at least one aqueous polyurethane dispersion to the at least one cross-linked starch is between 1.1 and 6.5.

11. The composition according to claim 1 which comprises a quantity of water from 30% to 95% by weight in relation to the total weight of the composition.

12. The composition according to claim 1 which further comprises hydrophobic particles.

13. The composition according to claim 1 which is substantially free of cationic surfactants and/or of any compound comprising at least one —$NH_3^+$ group.

14. A cosmetic method for caring of the skin and/or scalp, comprising the application to said skin and/or scalp of the composition according to claim 1.

15. The composition according to claim 2, wherein the at least one chain extender B) is an alkylene diamine chosen from the group consisting of hydrazine, ethylenediamine, propylenediamine, 1,4-butylenediamine and piperazine; or an alkylene oxide diamine chosen from the group consisting of 3-{2-[2-(3-aminopropoxy)ethoxy]ethoxy}propylamine, 2-methyl-1,5-pentanediamine, hexane diamine, isophorone diamine, and 4,4-methylenedi-(cyclohexylamine), dipropylamine propyleneglycol, dipropylamine dipropyleneglycol, dipropylamine tripropyleneglycol, dipropylamine poly (propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol.

16. The composition according to claim 3, wherein the at least one chain extender B) is an alkylene diamine chosen from the group consisting of hydrazine, ethylenediamine, propylenediamine, 1,4-butylenediamine and piperazine; or an alkylene oxide diamine chosen from 3-{2-[2-(3-aminopropoxy)ethoxy]ethoxy}propylamine, 2-methyl-1,5-pentanediamine, hexane diamine, isophorone diamine, and 4,4-methylenedi-(cyclohexylamine), dipropylamine propyleneglycol, dipropylamine dipropyleneglycol, dipropylamine tripropyleneglycol, dipropylamine poly(propylene glycol), dipropylamine ethyleneglycol, dipropylamine poly (ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol.

17. The composition according to claim 2, wherein the chain extender C) is chosen from the group consisting of the sodium salt of N-(2-aminoethyl)-2-aminoethane sulfonic acid, the sodium salt of N-(2-aminoethyl)-3-aminoethane sulfonic acid and the sodium salt of N-(2-aminoethyl)-2-aminopropionic acid.

\* \* \* \* \*